United States Patent
Pastorello et al.

(10) Patent No.: US 11,357,858 B2
(45) Date of Patent: Jun. 14, 2022

(54) PHARMACEUTICAL COMPOSITIONS FOR THE TREATMENT OF POSTOPERATIVE PAIN

(71) Applicant: FIDIA FARMACEUTICI S.P.A., Abano Terme (IT)

(72) Inventors: Andrea Pastorello, Abano Terme (IT); Fabio Bettella, Abano Terme (IT); Devis Galesso, Abano Terme (IT)

(73) Assignee: FIDIA FARMACEUTICI S.p.A., Abano Terme (IT)

( * ) Notice: Subject to any disclaimer, the term of this patent is extended or adjusted under 35 U.S.C. 154(b) by 10 days.

(21) Appl. No.: 16/964,542

(22) PCT Filed: Jan. 23, 2019

(86) PCT No.: PCT/IB2019/050552
§ 371 (c)(1),
(2) Date: Jul. 23, 2020

(87) PCT Pub. No.: WO2019/145863
PCT Pub. Date: Aug. 1, 2019

(65) Prior Publication Data
US 2020/0360519 A1   Nov. 19, 2020

(30) Foreign Application Priority Data
Jan. 25, 2018  (IT) .................. 102018000001890

(51) Int. Cl.
*A61K 47/36* (2006.01)
*A61K 9/00* (2006.01)
*A61K 31/445* (2006.01)

(52) U.S. Cl.
CPC ............ *A61K 47/36* (2013.01); *A61K 9/0019* (2013.01); *A61K 31/445* (2013.01)

(58) Field of Classification Search
None
See application file for complete search history.

(56) References Cited

FOREIGN PATENT DOCUMENTS

| EP | 0 341 745 A1 | 11/1989 |
|---|---|---|
| WO | WO 97/11681 A1 | 4/1997 |
| WO | WO 00/01733 A1 | 1/2000 |
| WO | WO 2010/015901 A1 | 2/2010 |
| WO | WO 2011/023355 A2 | 3/2011 |
| WO | WO 2012/014180 A1 | 2/2012 |
| WO | WO 2015/043757 A1 | 4/2015 |

OTHER PUBLICATIONS

International Search Report for PCT/IB2019/050552 (PCT/ISA/210) dated Mar. 26, 2019.
Written Opinion of the International Searching Authority for PCT/IB2019/050552 (PCT/ISA/237) dated Mar. 26, 2019.

*Primary Examiner* — Dale R Miller
(74) *Attorney, Agent, or Firm* — Birch, Stewart, Kolasch & Birch, LLP

(57) ABSTRACT

Disclosed are pharmaceutical compositions in gel form comprising a hydrophilic matrix consisting of a hyaluronic acid derivative containing an amide local anaesthetic in base form.

13 Claims, 2 Drawing Sheets

PHARMACEUTICAL COMPOSITIONS FOR THE TREATMENT OF POSTOPERATIVE PAIN

The invention relates to pharmaceutical compositions in gel form comprising an amide local anaesthetic.

PRIOR ART

Postoperative pain is a complex response to the tissue trauma caused by surgery, which induces hypersensitivity of the central nervous system. Postoperative pain can arise after any surgical procedure, and increases the risk of postoperative complications, also interfering with the patient's recovery and return to normal activities. The healing process is considerably slowed when the patient is unable to move independently, eat or sleep without feeling pain, as pain is also felt in areas distant from the site of the operation. Pain also induces a state of psychological prostration in the patient which further aggravates the overall clinical picture. Careful postoperative pain management is essential nowadays, and is strongly promoted by the World Health Organisation as it is considered to be a fundamental right of patients.

The perception of pain depends not only on the type of surgery (abdominal surgery and chest surgery are more painful than procedures involving the limbs, and abdominal or chest incisions cause even more intense pain when the peritoneum or pleura is involved), but also on subjective conditions, such as prior painful experiences, anxiety, and genetic predisposition; for this reason, healthcare personnel seek to implement analgesic measures by adapting them to the intensity reported by each patient, which can be correctly measured with the use of a pain assessment scale. The most widely used of the various scales available are one-dimensional scales, which are easily administered, and wherein the only parameter considered is the expression of the amount of pain perceived by the patient. The best-known are the NRS scale (Numerical Rating Scale—Downie et al, Ann Rheum Dis, 1978, 378-381), wherein the operator asks patients to express verbally the amount of pain they feel on a scale from 0 to 10 (0=no pain; 10=maximum pain), and the VAS scale (Visual Analogical Scale—Scott, Huskisson, Pain, 1976, 2, 175-184), wherein the pain felt is indicated by the patient on a line resembling a ruler, which is 10 cm long. This latter scale is widely used because it is easily understood by patients, including those of paediatric age. Other more complex scales are used for patients unable to express themselves, or those suffering from concomitant disorders which prevent correct verbal and/or motor expression.

Postoperative pain management is dependent on pharmacological treatment. To alleviate pain during and immediately after surgery, drugs are usually administered intravenously; the drugs are question are generally opioids, whose use is limited to fairly short periods because of their serious side effects.

When the patient is able to take them and the overall clinical picture so allows, drugs are then administered orally, such as paracetamol, traditional NSAIDs or COX-2, whose side effects are well known. A further approach to the treatment of postoperative pain involves a nerve block using local anaesthetics. Depending on the type of surgery, nerve block analgesia may be peripheral, when the anaesthetic is administered locally along the route of a nerve, or central, when the anaesthetic is administered close to the posterior spinal roots of the nerves. Peripheral analgesia relieves pain in the precise area of the body innervated by the specific nerve anaesthetised, such as the arm or leg, and is generally obtained by intradermal injections close to the nerve to be blocked; central analgesia acts in a much broader way, and is administered by injection into the epidural space through catheters or pumps, which can be left in situ for several days after surgery if required. However, this treatment is always commenced after surgery.

The local anaesthetics most commonly used in these cases are lidocaine, bupivacaine, etidocaine, ropivacaine and the like, commonly called "amide local anaesthetics". These lipophilic molecules are pharmacologically active in their base form which is able to penetrate the membranes of nerve cells, but are poorly water-soluble, and are therefore available on the market in their protonated and salified form (usually with hydrochloric acid), which is less active. Protonation takes place at the tertiary nitrogen atom which acquires a partly positive charge, and is therefore able to bond to an anion (usually chloride, as already stated). Local or central analgesia with local anaesthetics has a very short duration, due to the rapid resorption of the active ingredient into the bloodstream; the more vascularised the treated area, the faster the resorption. This can be remedied, especially for the peripheral block, by combining the local anaesthetic with a vasoconstrictor. In that event, however, repeated administrations at relatively short intervals are required. Moreover, in view of their liposolubility, amide local anaesthetics tend to accumulate in the fat present in the tissues, and repeated administrations or higher doses can therefore easily give rise not only to forms of dependence, but also to significant side effects, which may be neurological (drowsiness, feeling of intoxication, tinnitus, visual disorders, agitation to the point of convulsions, coma and cardiorespiratory depression) or cardiac (rhythm disorders, ventricular extrasystoles, ventricular and supraventricular tachycardia, and conduction disorders). In general, therefore, to achieve effective, lasting pain suppression while minimising the risks associated with the local anaesthetic, it tends to be combined with an oral NSAID in clinical practice.

To improve the duration of the analgesic effect, combinations of an anaesthetic with a carrier from which it is released have been studied.

In particular, combinations with hydrophobic carriers are known, due to their affinity with the active form of the active ingredient; for example, an injectable formulation has been devised based on biodegradable lipid microbeads incorporating bupivacaine, which is gradually released (Exparel®). The formulation can only be administered by injection and often induces redness, itching and erythema at the site of injection, but above all has a short-lived effect, not exceeding 24 hours. Other attempts have been made by using a matrix of polylactic acid, polyglycolic acid and the corresponding copolymers, polyorthoesters, etc., which are able to release a local anaesthetic combined with an NSAID. In this case, in view of the concomitant administration of two active ingredients, significant toxicity problems and adverse events can easily occur (US2017035777). Moreover, there is a possibility that the local anaesthetic may be retained in some way in a carrier which is chemically similar to it, with the risk of undesirable accumulations and a consequent alteration in the pharmacokinetic profile. To deal with this aspect, other attempts have been made using hydrophilic matrices wherein the local anaesthetic is incorporated in its hydrochloride form, which is less active but available on the market and similar to the nature of the matrix; for example, US2010266693 combines bupivacaine HCl with a matrix of hyaluronic acid and fibrinogen. Lu et al. (*Arch Med Sci*, 2013, 9, 614-621) describe the use of ropivacaine HCl together with hydrophilic polymers. Although the hydrophilic matrix exhibits better biocompatibility, incorporates the ropivacaine salt without difficulty and does not give rise to the accumulation effect, the results obtained in terms of efficacy and duration of analgesia are unsatisfactory: after an intense, undesirable initial burst, the analgesic effect wears off in a fairly short time, for the reasons already described.

DESCRIPTION OF THE INVENTION

Figure 1:
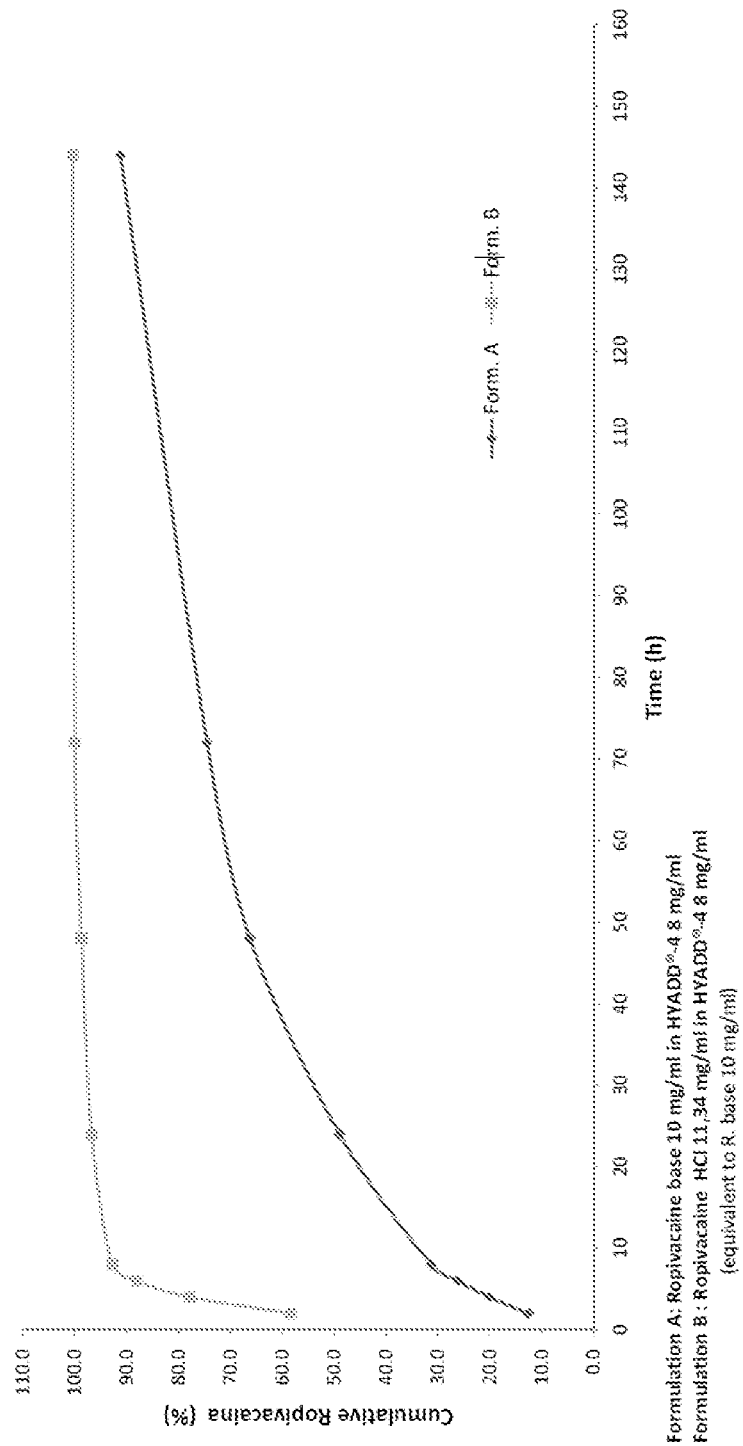
FIG. 1 shows the cumulative results of ropivacaine base vs. ropivacaine HCl release test from a HYADD®-4 carrier from Example 8.

It has now been discovered that slow release of an amide local anaesthetic can be obtained by incorporating it in a lipophilic, base form in a hydrophilic matrix comprising a hyaluronic acid derivative; in this context, "base form" means the non-protonated form.

The subject of the invention is therefore pharmaceutical compositions in gel form comprising a hydrophilic matrix consisting of a hyaluronic acid derivative containing an amide local anaesthetic in base form, and optionally containing known pharmaceutically acceptable excipients. The compositions according to the invention are particularly useful in the treatment of postoperative pain deriving from any kind of surgery, especially after orthopaedic surgery, and perform their analgesic activity for up to 5 days after application.

They can be administered at the time of surgery by various routes, for example by injection and/or infiltration into the tissues surrounding the surgical wound, by direct instillation into the open wound, or by simple topical application involving spreading. The analgesic effect continues for a surprisingly long time (up to 5 days), especially when the composition is administered in the tissues surrounding a wound, in particular in orthopaedic surgery wounds.

The invention also relates to the process for the preparation of said pharmaceutical compositions, which comprises adding the hyaluronic acid derivative to an aqueous suspension of the local anaesthetic in a non-protonated base form obtained by neutralising an aqueous solution of the salts, in particular the hydrochloride salt, of the local anaesthetic, with suitable bases.

The process, which can be performed by the "one-pot" procedure, traps the local anaesthetic in its active, lipophilic and base form in the mesh of the hydrophilic matrix consisting of the hyaluronic acid derivative.

A further subject of the invention is a controlled-release system (Drug Delivery System) comprising a matrix consisting of a hyaluronic acid derivative able to release a local anaesthetic in its base form in a controlled way, and further containing pharmaceutically acceptable excipients, known to the skilled person.

DETAILED DESCRIPTION OF THE INVENTION

Amide local anaesthetics comprise lidocaine, bupivacaine, etidocaine and ropivacaine. Ropivacaine is particularly preferred, due to its pharmacotoxicological characteristics.

Hyaluronic acid (HA) is a straight-chain heteropolysaccharide consisting of alternating residues of D-glucuronic acid and N-acetyl-D-glucosamine, having a molecular weight (MW) ranging between 50,000 and $13 \times 10^6$ Da, depending on the source from which it is obtained and the preparation methods used. "Average molecular weight" here means the weight-average molecular weight, calculated by the "intrinsic viscosity" method (Terbojevich et al., *Carbohydr Res*, 1986, 363-377).

Hyaluronic acid is ubiquitously present in the human body, wherein it performs a myriad of activities, ranging from mechanical support for the cells of many tissues, such as skin, tendons, muscles and cartilage, to modulation of the numerous different cell physiology and biology processes (proliferation, migration, cell differentiation and angiogenesis), tissue hydration and joint lubrication. More recently it was demonstrated that HA also acts as an anti-inflammatory by modulating the release of inflammatory cytokines, in particular IL-1, and is also able to bond to specific opioid receptors by mimicking an analgesic effect.

Due to its particular chemical structure, HA can be variously converted by means of suitable chemical reactions to derivatives that maintain the biological characteristics of the starting polymer, but are differentiated from it in physicochemical terms and are therefore suitable for numerous applications.

According to the invention, the hyaluronic acid derivative is selected from the following groups of derivatives:

autocrosslinked derivatives obtained by internal esterification, with a degree of esterification not exceeding 20%, preferably between 0.05 and 10%, and even more preferably between 4 and 5%, and prepared from HA with a weight average MW ranging between 160 and 230 kDa, preferably 200 kDa, hereinafter called "ACP®" (EP341745);

crosslinked derivatives, obtained by using crosslinking agents such as BDDE (1,4-butanediol diglycidyl ether), with a degree of derivatisation ranging between 2.5 and 25% molar, preferably between 5 and 15% molar (relative to the repeating unit of hyaluronic acid), and prepared from HA with a weight average MW ranging between 500 and 730 kDa, hereinafter called "HBC" (EP2470230);

amide derivatives, namely the amides between the HA carboxyl and the amino group of amines of the aliphatic, arylaliphatic, cycloaliphatic, aromatic, cyclic and heterocyclic series, with a degree of amidation ranging from 0.1 to 50%, and prepared from HA with a weight average MW ranging between 500 and 730 kDa, as described in EP1095064.

The amide derivatives of the aliphatic series are preferred, in particular hexadecyl, octadecyl or dodecyl amides, more preferably the hexadecyl amide prepared from an HA with a weight average MW ranging between 500 kDa and 730 kDa, and having an average degree of derivatisation (amidation) ranging between 0.1% and 10% molar, preferably between 1% and 3% molar, detected with HPLC after hydrolysis of the amide and conjugation of the hexadecylamine released with a fluorophoric substance. In the ambit of the present invention, the hexadecyl amide having the characteristics stated above and an average degree of derivatisation (amidation) ranging between 1% and 3% molar is called "HYADD®-4", and its preparation is described in EP1853279.

The derivatives described above, especially hexadecyl amide, are characterised by the ability to gel in aqueous solution even at low concentrations, forming a stable gel.

The resulting gel is exceptionally efficient at trapping the local anaesthetic in base form in its mesh and gradually releasing it; the anaesthetic released is converted very rapidly to the protonated form (a site that has undergone surgery is rich in acidic fluids, as a result of the inflammation induced by the surgical procedure and the physiological tissue repair mechanisms) and, as its activity wears off, is gradually replaced by another anaesthetic in base form released from the mesh of the gel. Moreover, the rheological characteristics of the gel facilitate the extrusion of the end product, making it possible to apply it with needles of small gauge and the application of reasonable force.

The combination of a hydrophilic HA derivative, especially the amide derivative HYADD®-4, and an amide local anaesthetic, in particular ropivacaine, in its base lipophilic form, without the addition of other active agents, gives rise to a surprisingly effective controlled-release system; the local anaesthetic in the form of a base is released from the hydrophilic matrix constantly and continuously, producing an effective analgesic effect which is much longer-lasting that obtainable with the salified form. Specifically, the release of ropivacaine base was evaluated with an in vitro test, illustrated below, by comparison with an equivalent composition containing the hydrochloride form. The comparison demonstrates that the composition according to the invention exercises its analgesic effect for up to 5 days.

The compositions according to the invention are prepared by converting the salts of the amide anaesthetic, in particular ropivacaine hydrochloride, to the corresponding bases, which therefore remain stably suspended in the matrix of the HA derivative in the form of a fine precipitate, and are released constantly and gradually.

In schematic form, the compositions according to the invention are prepared in the following steps:

solubilisation of the local anaesthetic in its salified form in an aqueous carrier, such as saline solution or PBS, preferably PBS, in a single portion or multiple portions; this reduces the pH of the solution, which becomes acidic; the pH value reached depends on the anaesthetic used;

precipitation of the local anaesthetic in its base form by treating the solution obtained in step a) with a base until pH values ranging between 6.5 and 8 are reached. The base can be a base containing an alkali metal or alkaline-earth metal, preferably an alkali metal, and even more preferably is NaOH;

addition to the resulting suspension of the chosen powdered hyaluronic acid derivative, leading to gel formation.

In particular, with specific reference to ropivacaine, after solubilisation of the hydrochloride in an aqueous carrier, with a consequent reduction of the pH to values below 6, treatment with a base converts the salt to the base, lipophilic, water-insoluble form, which therefore precipitates in a very fine form. The ropivacaine solubilisation stages and the subsequent precipitation can be completed in a single step (for ropivacaine HCl concentrations up to about 15-18 mg/ml) or can be fractionated into multiple steps, when higher concentrations are required. In this second case, the amounts of base, typically NaOH, which are added in each step are close to stoichiometric relative to ropivacaine HCl (so as to induce almost total precipitation thereof), maintaining the pH at values ranging between 6.5 and 8. Regardless of the number of steps performed, the precipitate obtained is left in suspension in its mother liquor, to which is added the selected hyaluronic acid derivative, preferably the amide HYADD®-4, as defined above, in powder form;

a stable, sterilisable gel is formed which incorporates the precipitate in its mesh and gradually releases it. The preparation is conducted with a one-pot reaction, which is extremely simple and short, without wastage of reagents and therefore economical from the industrial standpoint, and is perfectly replicable for all HA derivatives and all the local anaesthetics according to the invention.

The doses administered will clearly be customised on the basis of the extent of the surgery and the patient's general condition, obviously having regard to the necessary limits to prevent overdoses. In general, the hyaluronic acid derivative, in particular hexadecyl amide HYADD®-4, is prepared at a concentration ranging between 5 and 15 mg/ml, preferably between 7 and 12 mg/ml, and even more preferably is 8 mg/ml. The other HA derivatives according to the invention, namely the autocrosslinked derivatives ACP® and the crosslinked derivatives obtained with BDDE (HBC), are preferably used at concentrations ranging between 10 and 40 mg/ml, preferably between 20 and 30 mg/ml. Concentrations of HA derivatives ranging between 5 and 40 mg/ml produce a stable gel, which releases the active ingredient in a constant, prolonged way. In view of the prolonged release system, the local anaesthetic can be included in the carrier at different concentrations, which can be modulated as required. In particular for ropivacaine, the anaesthetic preferably used, and also for the other local anaesthetics described, the concentrations range between 10 and 35 mg/ml relative to the final composition, preferably 10 mg/ml, 15 mg/ml, 25 mg/ml or 35/mg/ml. Basically, with reference to a pharmaceutical composition as described based on HYADD®-4 8 mg/ml and ropivacaine base 35 mg/ml, each ml of final composition will contain 8 mg of HYADD®-4 and 35 mg of ropivacaine base.

Similar considerations to those expressed for HA derivatives and the local anaesthetic in base form used, and their concentrations, can also be extended to the controlled release system described above, comprising a matrix which will therefore preferably consist of hexadecyl amide of hyaluronic acid HYADD®-4 prepared at a concentration ranging between 5 and 15 mg/ml, preferably between 7 and 12 mg/ml, and even more preferably amounting to 8 mg/ml, and ropivacaine in base form at concentrations ranging between 10 and 35 mg/ml relative to the final composition, preferably amounting to 10 mg/ml, 15 mg/ml, 25 mg/ml or 35/mg/ml. As an alternative to HYADD®-4, the matrix of the controlled release system can consist of hyaluronic acid derivatives ACP® or HBC, as already described, at a concentration ranging between 10 and 40 mg/ml, preferably between 20 and 30 mg/ml, and a local anaesthetic, preferably ropivacaine, in base form, at the concentrations specified above.

The compositions according to the invention and the controlled release systems described above can be used in the treatment of postoperative pain, and have the following characteristics:

they are all biocompatible and biodegradable;
they consist of a hydrophilic matrix, which prevents abnormal accumulation of the active ingredient;
they are sterilisable by the classic methods (autoclave);
they are stable at room temperature and even at 40° for at least 6 months;
they are easily extruded with needles up to 27 G by application of reasonable pressure;
they can be administered by injection and/or infiltration into the tissues surrounding the surgical wound, by direct instillation into the open wound, and by simple topical application, for example by spreading on the edge of a prosthesis at the time of its implantation; the administration routes can also be combined, according to the type of surgery performed;

they are prepared in a very simple way by a one-pot reaction, and are therefore economical from the industrial standpoint;

the analgesic effect is maintained for up to 5 days, in particular when administered in the tissues surrounding a wound, especially in orthopaedic surgery wounds;

the compositions according to the invention can therefore be administered in a single dose at the time of surgery, and the concomitant use of NSAIDs or other oral painkillers can be dramatically reduced or even totally eliminated.

The compositions according to the invention are suitable for use as analgesics in numerous surgical applications, including:

orthopaedic surgery: such as total or partial knee or hip replacement, shoulder, ankle, hand or bunion surgery or foot surgery in general, spinal procedures, etc.;

abdominal surgery: such as herniectomy, appendicectomy, colectomy, gastric resection, colorectal surgery, etc.;

surgery of the urogenital tract (prostatectomy, nephrectomy, hysterectomy, oophorectomy, caesarean section), etc.;

vascular surgery (haemorrhoidectomy).

The following examples illustrate the invention in greater detail.

Example 1

Preparation of a HYADD®-4 (8 mg/ml) and Ropivacaine Base (15 mg/ml) Gel 79.6 ml of PBS 3 mM, pH 7.3±0.1, was poured into a 250 ml reactor equipped with a stirrer; 1.70 g of ropivacaine HCl was then added which, when it solubilised, adjusted the pH to about 5.7, and the mixture was maintained under stirring for at least 20 minutes. At this point, 0.4 M NaOH was added slowly under stirring until a pH of 7.2-7.4 was reached; the variation in pH led to the precipitation of ropivacaine in base form, giving rise to the formation of a very fine suspension.

After adjusting the suspension to a volume of 100 ml with PBS pH 7.3±0.1, 0.8 g of powdered HYADD®-4 was added in the reactor under stirring; stirring was maintained for about an hour, and the mixture was then left to stand for at least 3 hours. The resulting gelled suspension was mixed for at least 10 minutes, filtered through a stainless steel filter with a porosity of 105 and mixed again for at least a further 10 minutes. The gelled suspension was then used to fill syringes and sterilised in the autoclave.

Example 2

Preparation of a HYADD®-4 (8 mg/ml) and Ropivacaine Base (25 mg/ml) Gel 68 ml of PBS 3 mM, pH 7.3±0.1, was poured into a 250 ml reactor equipped with a stirrer; 1.40 g of ropivacaine HCl was then added which, when it solubilised, adjusted the pH to about 5.8, and the mixture was maintained under stirring for at least 20 minutes.

At this point, 9.6 ml of 0.4 M NaOH was added slowly under stirring, to obtain a first precipitate of ropivacaine base.

A further 1.43 g of ropivacaine HCl was added, with a corresponding reduction of the pH to about 5.8, and stirring was maintained for 20 minutes. At this point, 0.4 M NaOH was added slowly under stirring until a pH of 7.2-7.4 was reached, to obtain a very fine suspension of ropivacaine base.

After adjusting the suspension to a volume of 100 ml with PBS pH 7.3±0.1, 0.8 g of powdered HYADD®-4 was added in the reactor under stirring; stirring was maintained for about an hour, and the mixture was then left to stand for at least 3 hours. The resulting gelled suspension was mixed for at least 10 minutes, filtered through a stainless steel filter with a porosity of 105 µm, and mixed again for at least a further 10 minutes. The gelled suspension was then used to fill syringes and sterilised in the autoclave.

Example 3

Preparation of a HYADD®-4 (8 mg/ml) and Ropivacaine Base (35 mg/ml) Gel 64 ml of PBS 3 mM, pH 7.3±0.1, was poured into a 250 ml reactor equipped with a stirrer; 1.40 g of ropivacaine HCl was then added which, when it solubilised, adjusted the pH to about 5.7, and the mixture was maintained under stirring for at least 20 minutes.

9.6 ml of 0.4 M NaOH was added slowly under stirring, to obtain a first precipitate of ropivacaine base.

A further 1.40 g of ropivacaine HCl was added which again reduced the pH to acid values (about 5.8), and stirring was maintained for 20 minutes; 9.6 ml of 0.4 M NaOH was then added slowly under stirring.

A further 1.16 g of ropivacaine HCl was added, and the resulting acid solution (pH about 5.8) was maintained under stirring for 20 minutes.

At this point, 0.4 M NaOH was added slowly under stirring until a pH of 7.2-7.4 was reached, to obtain a very fine suspension of ropivacaine base.

After adjusting to a volume of 100 ml with PBS pH 7.3±0.1, 0.8 g of powdered HYADD®-4 was added in the reactor under stirring; stirring was maintained for about an hour, and the mixture was then left to stand for at least 3 hours. The resulting gelled suspension was mixed for at least 10 minutes, filtered through a stainless steel filter with a porosity of 105 µm, and mixed again for at least a further 10 minutes. The gelled suspension was then used to fill syringes and sterilised in the autoclave.

Example 4

Preparation of a HYADD®-4 (8 mg/ml) and Ropivacaine Base (10 mg/ml) Gel 80 ml of PBS 3 mM, pH 7.3±0.1, was poured into a 250 ml reactor equipped with a stirrer; 1.134 g of ropivacaine HCl was then added which, when it solubilised, adjusted the pH to about 5.8, and the mixture was maintained under stirring for at least 20 minutes. At this point, 0.4 M NaOH was added slowly under stirring until a pH of 7.2-7.4 was reached; the variation in pH led to the precipitation of ropivacaine in base form, giving rise to the formation of a very fine suspension.

After adjusting the suspension to a volume of 100 ml with PBS pH 7.3±0.1, 0.8 g of powdered HYADD®-4 was added in the reactor under stirring; stirring was maintained for about an hour, and the mixture was then left to stand for at least 3 hours. The resulting gelled suspension was mixed for at least 10 minutes, filtered through a stainless steel filter with a porosity of 105 μm, and mixed again for at least a further 10 minutes. The gelled suspension was then used to fill syringes and sterilised in the autoclave.

Example 5

Preparation of a HYADD®-4 (8 mg/ml) and Bupivacaine Base (15 mg/ml) Gel 79.6 ml of PBS 3 mM, pH 7.3±0.1, is poured into a 250 ml reactor equipped with a stirrer; 1.69 g of bupivacaine HCl is then added, and the mixture is maintained under stirring for at least 20 minutes.

The pH of the mixture has a value of 5.8. At this point, 0.4 M NaOH is added slowly under stirring until a pH of 7.2-7.4 is reached; the variation in pH leads to the precipitation of bupivacaine in base form, giving rise to the formation of a very fine suspension.

After adjusting to a volume of 100 ml with PBS pH 7.3±0.1, 0.8 g of powdered HYADD®-4 is added in the reactor under stirring; stirring is maintained for about an hour, and the mixture is then left to stand for at least 3 hours. The resulting gelled suspension is mixed for at least 10 minutes, filtered through a stainless steel filter with a porosity of 105 μm, and mixed again for at least a further 10 minutes. The gelled suspension is then used to fill syringes and sterilised in the autoclave.

Example 6

Preparation of a HYADD®-4 (8 mg/ml) and Bupivacaine Base (35 mg/ml) Gel 64 ml of PBS 3 mM, pH 7.3±0.1, is poured into a 250 ml reactor equipped with a stirrer; 1.40 g of bupivacaine HCl is then added, and the mixture is maintained under stirring for at least 20 minutes.

The pH of the mixture is 5.9. 9.1 ml of 0.4 M NaOH is added slowly, under stirring, to obtain a first precipitate of bupivacaine in base form.

A further 1.40 g of bupivacaine HCl is added, and the mixture is maintained under stirring for 20 minutes; the pH of the mixture is 5.9.

9.1 ml of NaOH 0.4 M is then added slowly, under stirring.

A further 1.14 g of bupivacaine HCl is added, with a consequent reduction of the pH to about 5.9, and the mixture is maintained under stirring for 20 minutes. At this point, 0.4 M NaOH is added slowly under stirring until a pH of 7.2-7.4 is reached, to obtain a very fine suspension of bupivacaine base.

After adjusting to a volume of 100 ml with PBS pH 7.3±0.1, 0.8 g of powdered HYADD®-4 is added in the reactor under stirring; stirring is maintained for about an hour, and the mixture is then left to stand for at least 3 hours. The resulting gelled suspension is mixed for at least 10 minutes, filtered through a stainless steel filter with a porosity of 105 and mixed again for at least a further 10 minutes. The gelled suspension is then used to fill syringes and sterilised in the autoclave.

Example 7

Preparation of an ACP® (20 mg/ml) and Ropivacaine Base (15 mg/ml) Gel 80.0 ml of 1.5 mM PBS solution, pH 6.9±0.1, is poured into a 250 ml reactor equipped with a stirrer; 1.70 g of ropivacaine HCl is added, and the mixture is maintained under stirring for at least 20 minutes. The pH of the mixture has a value of 5.7.

At this point, 0.4 M NaOH is added slowly under stirring until a pH of 6.8-7.0 is reached; the variation in pH leads to the precipitation of ropivacaine in base form, giving rise to the formation of a very fine suspension.

After adjusting to a volume of 100 ml with PBS 0.5 mM, pH 6.9±0.1, 2.0 g of ACP® powder, with a degree of esterification amounting to 4.3%, is added in the reactor, under stirring.

Stirring is maintained for about an hour, and the mixture is then left to stand for at least 3 hours.

The resulting gelled suspension is mixed for at least 10 minutes, filtered through a stainless steel filter with a porosity of 105 μm, and mixed again for at least a further 10 minutes. The gelled suspension is then used to fill syringes and sterilised in the autoclave.

Example 8

Preparation of an HBC (20 mg/ml) and Ropivacaine Base (25 mg/ml) Gel 75 ml of PBS 3 mM, pH 7.3±0.1, is poured into a 250 ml reactor equipped with a stirrer; 1.4 g of ropivacaine HCl is added, and the mixture is maintained under stirring for 20 minutes; the pH of the mixture is 6.0.

9.6 ml of 0.4 M NaOH is added slowly, under stirring, to obtain a first precipitate of ropivacaine base.

A further 1.43 g of ropivacaine HCl is added, and the mixture is maintained under stirring for 20 minutes; the pH of the mixture is 6.0.

At this point, 0.4 M NaOH is added slowly under stirring until a pH of 7.2-7.4 is reached, obtaining a very fine suspension of ropivacaine base. The volume is adjusted to 100 ml with PBS 3 mM, pH 7.3±0.1, and 2.0 g of HBC powder with a degree of derivatisation of about 5.5% molar is then added. The mixture is heated to 60° C., and then maintained under stirring for 5 hours to allow the HBC powder to gel; it is then cooled to 20° C.

The resulting gelled suspension is mixed for at least 10 minutes, filtered through a stainless steel filter with a porosity of 105 μm, mixed again for at least another 10 minutes, and finally used to fill syringes and sterilised in the autoclave.

Ropivacaine base vs. ropivacaine HCl release test from a HYADD®-4 carrier.

The test was conducted with a classic release test apparatus, consisting of a donor compartment and a receiver compartment. In this specific case, the donor compartment is a container (Spectra/Por Float-A-Lyzer) which houses 1 ml of sample to be analysed, and is closed with a dialysis membrane with a cut-off of 100 kDa; the receiver compartment is a 50 ml test tube containing 15 ml of extraction solvent (PBS pH 7.0±0.1) and a magnetic anchor. After loading the donor compartment with the formulation to be analysed and inserting the donor into the receiver, the assembly is placed in a chamber thermostated to 37°, under gentle stirring. The samples analysed were:

Formulation A: ropivacaine base 10 mg/ml in HYADD®-4 8 mg/ml, prepared as described in Example 4;

Formulation B: ropivacaine HCl 11.34 mg/ml (equivalent to ropivacaine base 10 mg/ml) in HYADD®-4 8 mg/ml, prepared according to Example 4 simply by omitting the basification stage with NaOH.

The test was conducted in sink condition; in other words, at preset times the extraction solvent was completely replaced with an equal volume of "fresh" solvent to prevent the progressive increase in the concentration of the species to be tested in the extraction solvent from influencing its further release, thus altering the test results. In this specific case the extraction solvent was replaced after 2, 4, 6, 8, 24, 48, 72 and 144 hours, and the ropivacaine concentration was measured on each volume replaced; the cumulative results are set out in FIG. 1.

As will be seen, there is a great difference in behaviour between the two Formulations.

Formulation A according to the invention releases the ropivacaine base in a gradual, constant, continuous, prolonged way, until its effect has been exhausted, i.e. releasing substantially all the initial ropivacaine after about 140 hours (5 days).

Conversely, Formulation B releases ropivacaine HCl very rapidly; after 8 hours it has released over 90% of the anaesthetic, and after 24 hours no less than 98%, so that its effect is practically exhausted.

Bearing in mind that the matrix of the two formulations is identical (HYADD®-4 at the same concentrations) and the concentration of the anaesthetic is equivalent, the test unequivocally demonstrates that the innovative combination of the hydrophilic matrix consisting of an amide derivative of hyaluronic acid and ropivacaine, in base form and lipophilic, is exceptionally efficient in releasing the local anaesthetic in a gradual, constant, lasting way, thus ensuring lengthy painkilling coverage.

The experimental findings thus obtained were confirmed by preclinical efficacy tests conducted on animals, as described below.

Assessment of the Analgesic Effect of Ropivacaine Base in a HYADD®-4 Carrier vs Ropivacaine HCl The study was conducted on pigs, treated as established by the Laboratory Animal Care and Use Ethics Commission. The model applied is the Brennan postoperative pain assessment model (Brennan T J et al, *Pain,* 1996, 64, 493-501). It provides for a 1 cm longitudinal incision to be made in the skin of the animal, which cuts through the skin, fascia and underlying muscle; after stitching, at established intervals, postoperative pain is measured according to the von Frey method, by applying to the animal's skin filaments of known diameter, to which a force is applied until the perceived pain triggers the animal's reaction. The lower the pain perceived, the higher the force applied will be, expressed in grams/mm$^2$ (g); thus at baseline (before the incision) the force values will be high; after the incision, less force will be needed to induce a pain reaction in the animal. Thus the stronger the force that has to be applied to the Von Frey filament to trigger the animal's reaction, the greater the analgesic effect of the species tested.

The doses to be administered for each of the species tested were established on the basis of the know-how of the skilled person, as follows:

the maximum dose of ropivacaine HCl which can be administered without the onset of side effects is about 2.5 mg/kg (Srichartz G R, Berde C B, in: Miller R D, ed. Miller's Anesthesia. 6th ed. Philadelphia: Elsevier Churchill Livingstone, 2005: 573-603). Specifically, therefore, as the weight of each pig used in the study was about 10 kg, 2.5 ml of Naropin® (ropivacaine HCl 10 mg/ml) was used, equivalent to 25 mg of ropivacaine per animal;

in the comparison tests reported in the literature (Davidson E M et al, Anesth Analg, 2016, 122, 1663-72), ropivacaine in a lipophilic carrier was prepared in the ratio of 8:1 relative to the hydrochloride form in aqueous solution. Such high doses are necessary to test controlled release, as the local anaesthetic in protonated form is metabolised very quickly, as known, and ceases to act. This indication was therefore followed, administering to each animal a dose of the pharmaceutical composition to be tested containing 8 times the amount of ropivacaine HCl, i.e. the equivalent of 200 mg of ropivacaine HCl. As the pharmaceutical compositions tested contained different concentrations of ropivacaine base, the volume of each composition exactly corresponding to the established dose of ropivacaine HCl (200 mg) was calculated, and the volumes administered were therefore obviously different.

30 pigs were used, divided into 5 groups of 6, as follows:

Group 1: the animals were treated with the carrier, namely with 11.76 ml of HYADD®-4 (8 mg/ml), and constitute the negative control;

Group 2: the animals were treated with 11.76 ml of HYADD®-4 8 mg/ml containing ropivacaine base 15 mg/ml in quantity equal to 200 mg of ropivacaine HCl, prepared as described in Example 1;

Group 3: the animals were treated with 7.06 ml of HYADD®-4 8 mg/ml containing ropivacaine base 25 mg/ml in quantity equal to 200 mg of ropivacaine HCl, prepared as described in Example 2;

Group 4: the animals were treated with 5.05 ml of HYADD®-4 8 mg/ml containing ropivacaine base 35 mg/ml in quantity equal to 200 mg of ropivacaine HCl, prepared as described in Example 3;

Group 5: the animals were treated with 2.5 ml of Naropin® (ropivacaine HCl 10 mg/ml) in aqueous solution, equal to 25 mg of ropivacaine HCl, and constitute the positive control.

The treatments were given before the wound was stitched, by injecting half the volume into the wound site and half into the tissue surrounding the wound, at three different levels.

The von Frey test was applied at baseline, i.e. before the incision, and subsequently 3, 8, 12, 24, 36, 48 and 72 hours after surgery. The test results are set out in FIG. 2. The values are statistically significant.

It is absolutely evident that:

as expected, the carrier has no effect;

the effect of Naropin® is relatively good after 3 hours, very slight after only 8 hours, and non-existent in the subsequent hours;

the pharmaceutical composition tested containing HYADD®-4, at all the concentrations of ropivacaine used, has an intense painkilling activity, which for some concentrations is much higher (Group 2) than, or in any event similar to, that of Naropin® 3 hours after treatment, and much higher at the later times. Increased time reduces the painkilling effect of the compositions at a lower concentration of ropivacaine (Groups 2 and 3) and increases that of the species at a higher concentration (Group 4). This further demonstrates the efficacy of the controlled release system described in the invention.

Figure 2:
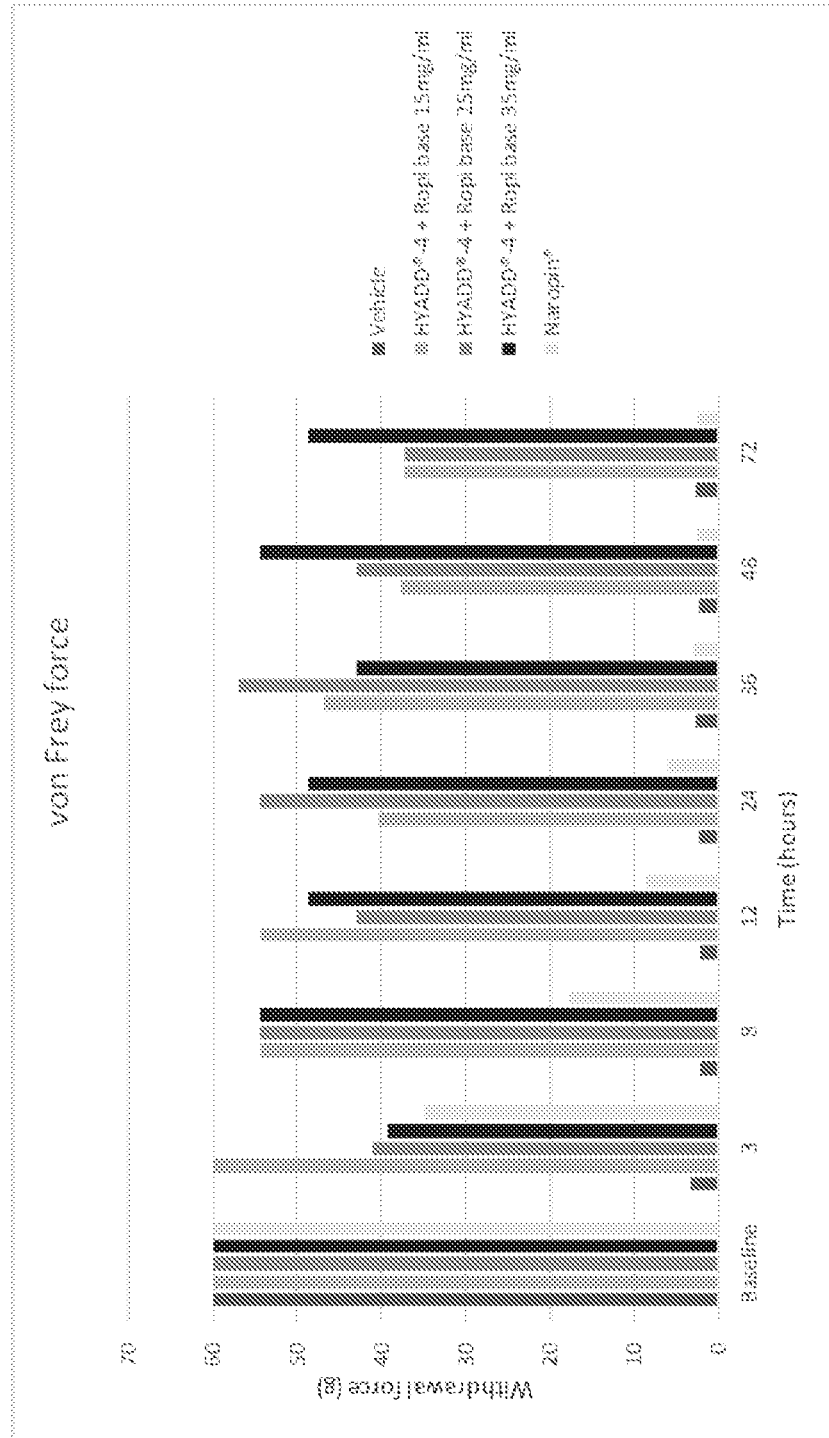
FIG. 2 shows the results of the von Frey test from Example 8.

Although the administration of the von Frey test was stopped for ethical reasons after 72 hours (3 days), the data in FIG. 2, analysed together with those of the release curve in FIG. 1, indicate that the painkilling efficacy of the species tested would be maintained for a long time thereafter since, for example, the species at the maximum concentration of ropivacaine (Group 4) has a very strong analgesic effect 72 hours after treatment: a force about 80% higher than that needed at baseline is required to induce the pain stimulus in the animal. This aspect is important, because it means that the amount of ropivacaine can be modulated on the basis of the duration of the desired painkilling effect, depending on the surgical operation the patient is to undergo, and other clinical considerations.

In addition to these results, which unequivocally demonstrate the long-term efficacy of the pharmaceutical compositions according to the invention, it should be noted that none of the treated animals had adverse reactions caused by ropivacaine overdose, although the dose of active ingredient globally administered was much higher than the standard dose of the hydrochloride form.

This means that the pharmaceutical compositions tested here:
- act as a controlled release system (Drug Delivery System) for the local anaesthetic, prolonging its analgesic effect over time;
- do not give rise to overdose and/or accumulation, and therefore prevent the well-known toxic side effects;
- eliminate the need for repeated administrations
- allow the duration of the painkilling effect to be modulated and thus represent a definite improvement on the state of the art in the treatment of postoperative pain.

The invention claimed is:

1. A method of treating postoperative pain, which comprises administering to a patient in need thereof a pharmaceutical composition, in gel form, comprising a hydrophilic matrix comprising a hyaluronic acid derivative containing an amide local anesthetic in base form, and optionally containing pharmaceutically acceptable excipients, wherein the hyaluronic acid derivative is selected from amide derivatives obtained by amidation of the carboxyl groups of hyaluronic acid and the amino groups of amines of the hexadecyl, octadecyl or dodecyl aliphatic series, with a degree of amidation ranging between 0.1 and 50% molar, and prepared from HA with a weight average MW ranging between 500 and 730 kDa; and the amide local anesthetic is selected from bupivacaine, etidocaine and ropivacaine.

2. The method according to claim 1, wherein the amide local anesthetic is ropivacaine.

3. The method according to claim 1, wherein the hyaluronic acid derivative is hexadecyl amide prepared from a hyaluronic acid with a weight average molecular weight ranging from 500 to 730 kDa, and having an average degree of amidation ranging from 0.1% to 10% molar.

4. The method according to claim 1, wherein the concentration of the hyaluronic acid derivative is between 5 and 40 mg/ml.

5. The method according to claim 1, wherein the concentration of the local anesthetic in base form ranges from 10 to 35 mg/ml.

6. The method according to claim 1, wherein the hyaluronic acid derivative is hexadecyl amide prepared from a hyaluronic acid with a weight average molecular weight ranging from 500 to 730 kDa and having an average degree of amidation ranging from 1 to 3% molar and a concentration between 5 and 15 mg/ml, and the local a anesthetic in base form is ropivacaine at a concentration between 10 and 35 mg/ml.

7. The method according to claim 1, wherein the composition releases the local anesthetic in a lipophilic and base form for a period of up to five days.

8. The method according to claim 2, wherein the concentration of the hyaluronic acid derivative is between 5 and 40 mg/ml.

9. The method according to claim 3, wherein the concentration of the hyaluronic acid derivative is between 5 and 40 mg/ml.

10. The method according to claim 3, wherein the average degree of amidation ranges from 1 to 3% molar.

11. Controlled release system comprising a matrix comprising a hyaluronic acid derivative and an amide local anesthetic in base form, wherein the hyaluronic acid derivative is selected from amide derivatives obtained by amidation of the carboxyl groups of hyaluronic acid and the amino groups of amines of the hexadecyl, octadecyl or dodecyl aliphatic series with a degree of amidation ranging from 0.1 to 50% molar, prepared from HA with a weight average MW ranging between 500 and 730 kDa; and wherein the amide local anesthetic is selected from bupivacaine, etidocaine and ropivacaine.

12. Controlled release system as claimed in claim 11 wherein the hyaluronic acid derivative is hexadecyl amide prepared from a hyaluronic acid with a weight average molecular weight ranging between 500 and 730 kDa and having an average degree of amidation ranging between 1 and 3% molar and a concentration ranging between 5 and 15 mg/ml, and the local anesthetic in base form is ropivacaine at a concentration ranging between 10 and 35 mg/ml.

13. Process for the preparation of a controlled release system comprising a matrix comprising a hyaluronic acid derivative and an amide local anaesthetic in base form, which comprises:
- solubilizing the local anesthetic in its salified form in a single portion or in several portions in an aqueous carrier;
- precipitating the local anesthetic in its base form by treating the solution obtained in the previous step with a base, up to pH values ranging from 6.5 to 8;
- adding the hyaluronic acid derivative to the resulting suspension;

wherein the hyaluronic acid derivative is selected from: amide derivatives obtained by amidation of the carboxyl groups of hyaluronic acid and the amino groups of amines of the hexadecyl, octadecyl or dodecyl aliphatic series, with a degree of amidation ranging from 0.1 to 50% molar, prepared from HA with a weight average MW ranging between 500 and 730 kDa; and wherein the amide local anesthetic is selected from bupivacaine, etidocaine and ropivacaine.

* * * * *